United States Patent [19]
Alkafeef

[11] Patent Number: 5,831,721
[45] Date of Patent: Nov. 3, 1998

[54] METHOD AND APPARATUS FOR MEASURING PARTICLE SIZE DISTRIBUTION IN FLUIDS

[76] Inventor: Saad Feheid Mutlaq Alkafeef, P.O. Box 88700, Steilacoom, Wash. 98388

[21] Appl. No.: 654,584

[22] Filed: May 29, 1996

[51] Int. Cl.[6] ............................................. G01N 33/28
[52] U.S. Cl. ........................ 356/70; 356/336; 356/342
[58] Field of Search ........................ 356/336, 342, 356/70

[56] References Cited

U.S. PATENT DOCUMENTS

| | | | |
|---|---|---|---|
| 4,628,204 | 12/1986 | Maes | 356/70 |
| 4,641,969 | 2/1987 | Lunberg et al. | 356/342 |
| 4,707,134 | 11/1987 | McLachlan et al. | 356/342 |
| 4,715,711 | 12/1987 | Dunn | 356/342 |
| 5,365,326 | 11/1994 | Chrisman et al. | 356/246 |

OTHER PUBLICATIONS

Thomas et al "Experimental and theoretical studies of solids precipitation from reservoir fluid" *Journal of Canadian Petroleum Technology*, vol. 31, No. 1, pp. 22–31, Jan. 1992.

MacMillan et al. "A Unified Approach to Asphaltene Precipitation: LaLoratory Measurement and Modeling". SPE 28990. pp. 471–480, Feb. 1995.

*Primary Examiner*—Richard A. Rosenberger
*Attorney, Agent, or Firm*—Shlesinger Arkwright & Garvey LLP

[57] ABSTRACT

Methods and apparatus utilizing back scattered laser light measurement techniques for the measurement of particle size distribution in a fluid are disclosed. Such methods and apparatus are particularly suited for but not limited to the measurement of sub-micron particle size distribution in fluids such as petroleum fluids which are colored or opaque and strongly absorptive of incident light. Utilizing an optical transceiver partly immersed in the fluid, the methods and apparatus include provision for the measurement of particle size distribution while the fluid is subjected to conditions of high pressure and/or high temperature.

14 Claims, 3 Drawing Sheets

METHOD AND APPARATUS FOR MEASURING PARTICLE SIZE DISTRIBUTION IN FLUIDS

FIELD OF THE INVENTION

This invention relates to the measurement of particle size distribution in fluids, and is particularly adapted for the measurement of sub-micron particle size distribution in colloidal dispersions such as petroleum fluids.

BACKGROUND TO THE INVENTION

In the petroleum industry, the coagulation and deposition of asphaltene particles and wax (paraffin) crystallization (cloud-point) from petroleum fluid are costly problems. The particles of these two phenomena exist per se in sub-micron size under oil reservoir conditions. But, for reservoir engineers, the coagulation and deposition of asphaltene particles deep in a petroleum reservoir represents formation damage which may pose a threat to water drive mechanisms and impair the efficiency of oil recovery. Whereas, for petroleum production engineers, wax crystallization and asphaltene coagulation and deposition represent a threat to the integrity of oil well bores, well tubing and surface equipment.

The physics and chemistry of petroleum fluids is very complex and is not fully understood. However, it is generally accepted that asphaltene coagulation and deposition occurs as the result of changes in parameters such as pressure, temperature, and oil composition. As well, it may be influenced by electrical charge on particles. More particularly, it is believed that asphaltenes exist in oil as particles in a dispersed state, colloidally stabilized by petroleum resin molecules which form a layer or shield around asphaltene particles. The adsorption of resins on the surface of asphaltene particles is a function of resin concentration in the liquid phase. Thus, the changing of resin concentration will affect resin adsorption and the degree of coagulation. When the resin layer is removed by dissolution of the resin, the asphaltene particles will begin to aggregate (i.e. coagulate) into larger particles which can result in asphaltene deposition.

The crystallization point of wax or paraffin, also known as wax cloud-point, represents the temperature at which wax or paraffin begins to crystallize from a petroleum fluid. There are conventional American Society for Testing & Material (ASTM) procedures for predicting and determining wax cloud-point. However, the use of these procedures is limited or not applicable, especially in the case of dark crude oils.

Accordingly, it will be apparent that knowledge of wax crystallization characteristics and asphaltene particle size distribution in a petroleum fluid is important to petroleum engineers. With knowledge of the distribution and how it may change under differing conditions of temperature, pressure and other mechanical or chemical conditions, problems in the recovery or processing of the petroleum can be better foreseen, and steps may be taken to lessen or to avoid conditions which may favor the crystallization and coagulation of wax and asphaltene, respectively.

Over the years, known techniques have been devised whereby particle size distribution in a fluid is determined by detecting and analyzing light scattered by the fluid from an incident light signal of known intensity. However, with the methods and apparatus available, the utility of these techniques has been limited, particularly in cases where the fluid is colored or opaque and strongly absorptive of the incident light. In such cases, the intensity of the scattered light may be degraded below limits which may be readily detected and analyzed. Such is the case with petroleum fluids.

Until fairly recently, light scattering studies to obtain particle size distribution in colloidal dispersions were conducted in a "time average" mode where it was necessary to measure the intensity of light scattered at some angle $\Theta$ ($<90°$) from a straight through direction, and relate this to the incident intensity. Rather complex theory (Mie theory) was used to obtain particle size data and it was critically necessary to know the refractive index of the particles. In utilizing such an approach where an incident light signal is directed straight through the media (viz. from one side to the other), the optical path length in the fluid is necessarily maximized. This consequence is obviously disadvantageous if the media is strongly absorptive of the light because the intensity of the scattered light necessarily will be degraded.

With the advent of lasers, more powerful light beams became available. To a degree, this served to mitigate the difficulties associated with excessive optical path lengths. However, the time average technique itself was found to have limitations because it did not take advantage of the coherent, frequency stable characteristics of the laser. But, these characteristics have been exploited in a known technique variously referred to as intensity fluctuation spectroscopy ("IFS"), quasi-elastic life scattering ("QELS"), or, perhaps most frequently, photon correlation spectroscopy ("PCS").

With PCS, absolute intensities need not be measured. Instead, frequency shifts which arise from the (quasi-elastic) scattering of a laser beam from moving particles (Doppler effect) are detected. The movement may be systematic as in electrophoretic drift or random as in Brownian motion, the latter being exploited in a known manner for size distribution analysis.

The PCS technique is considered superior to the time average technique because it is not necessary to know the refractive index of particles in the dispersion and because it is not necessary to measure the intensity of light in or out of a fluid sample. But, it is necessary to measure the change of frequency from an incident light signal to that of light scattered back from particles in the fluid. However, with colored or opaque fluids, measurements still will be degraded if the optical path length defined in the fluid is excessive. Hence, there has evolved the development of optical back scatter techniques using PCS where incident light directed at a fluid is scattered back from a scattering volume defined just within the fluid at a distance which may be significantly less than the distance through the fluid from one side to the other.

Apparatus which enables the measurement of particle size distribution in fluids utilizing PCS with back scatter detection and analysis is known and commercially available. One manufacturer or supplier of such apparatus is Brookhaven Instruments Corp. of Holtsville, N.Y. Brookhaven offers an instrument known as a sub-micron particle analyzer which serves both to generate a laser light signal to be directed at a fluid sample and to receive and to analyze light which is scattered back from a scattering volume within the sample. The analysis is performed in conjunction with a digital computer and software provided by Brookhaven which processes signal information from the particle analyzer.

To use the Brookhaven instrument, the fluid sample is held in a transparent cell or container made from clear plastic or the like. A laser light signal generated by the instrument is transmitted and directed at the sample from an output at the tip or focusing end of a transceiving optical probe positioned outside the container wall. Light scattered back from a scattering volume in the sample on which the tip is focused is received at an input positioned at the same tip. Particle size distribution is determined with the Brookhaven instrument from this input.

Despite the relative sophistication of such instrumentation, the measurement of particle size distribution in the foregoing manner remains difficult or impossible if the fluid has strongly absorbing characteristics like that of petroleum fluid. Accurate measurements are compromised because a considerable amount of light is absorbed and the intensity of back scattered light can be very weak. In the case Brookhaven, the optical probe with the shortest focus or center point distance from the probe tip to the center of the scattering volume appears to be one where the distance is about 4 mm (viz. about 0.16 inches). If, for example, the fluid is a medium light crude oil, then this distance is too far. Useful measurements cannot be made because too much light is absorbed by the fluid. In general with such probes, the shortest possible focus distance will be limited by the wall thickness of the container which holds the fluid.

The foregoing difficulties become compounded if, as may often be the case with petroleum fluids, measurements are desired under non-ambient conditions of temperature and pressure.

Accordingly, a primary object of the present invention is to provide new and improved methods and apparatus utilizing back scattered light measurement techniques for the measurement of particle size distribution in fluids.

A further object of the present invention is to provide new and improved methods and apparatus utilizing back scattered light measurement techniques for the measurement of submicron particle size distribution in fluids such as petroleum fluids which are colored or opaque and strongly absorptive of incident light.

A still further object of the present invention is to provide new and improved methods and apparatus for the measurement of particle size distribution in fluids while the fluid are subjected to conditions of high pressure and/or high temperature.

SUMMARY OF THE INVENTION

In accordance with a broad aspect of the present invention, there is provided a method of measuring particle size distribution in a fluid, the method comprising the steps of holding the fluid in a container, directing an incident laser light signal to a scattering volume defined within the contained fluid from an optical transceiver at least partially immersed by the fluid, and detecting light scattered back to the transceiver from the scattering volume in response to the light signal.

The foregoing method may be applied to the measurement of particle size distribution in various fluids, but is particularly suitable for measuring sub-micron particle size distribution in colored or opaque fluids such as petroleum fluids where asphaltene particle size distribution and wax crystallization characteristics are of considerable interest. With the transceiver partially immersed by the fluid, the incident light signal may be directed to a scattering volume in the fluid very close to the transceiver. Hence, a minimal amount of light is absorbed by the fluid and a more readable amount of light is scattered back.

Advantageously, the fluid may be held in the container under controlled physical conditions (e.g. temperature and/ or pressure) which may affect fluid characteristics, and/or controlled chemical conditions (e.g. the addition of a solvent) which may also affect fluid characteristics. In the case of petroleum fluids, such conditions may be controlled to approximate that of a petroleum field reservoir from which the fluid is drawn, or conditions which may prevail or which may be contemplated at various points along the path of fluid recovery and processing. If, as will be evident from the measurement of particle size distribution, the conditions appear to favour asphaltene coagulation and deposition or wax coagulation, then the conditions can be varied to determine if the problem will be lessened or avoided. This knowledge will be of value to those who design and engineer the fluid recovery and processing system.

In another aspect of the present invention, there is provided apparatus for measuring particle size distribution in a fluid, such apparatus comprising a container for holding the fluid, an optical transceiver, and means for mounting the transceiver to the container in a position for directing an incident laser light signal from the transceiver to a scattering volume defined within the contained fluid and for detecting light scattered back to the transceiver from the scattering volume in response to the light signal. When so mounted, the transceiver is at least partially immersed by the fluid.

In a preferred embodiment, the mounting means comprises means for securing the transceiver in an opening extending through a wall of the container, the securing means including means for engaging the wall and the transceiver to seal the opening against passage of fluid from the container. Further, the apparatus advantageously includes means for controlling the pressure and/or temperature of the fluid within the container.

In a further aspect of the present invention, there is provided apparatus for measuring particle size distribution in a fluid, the apparatus comprising an optical window having first and second window surfaces, a housing having first and second ends and an inside and an outside extending between such ends, and transmitting and receiving optical fibre means extending inside the housing. The housing includes means proximate to the first end for holding the window with the first window surface facing outside the housing and the second window surface facing inside the housing. A sealing means is provided for sealing the window against the passage of fluid into said housing when the first window surface is immersed by the fluid, the fluid exerting a pressure on the housing and the first window surface substantially greater than the pressure inside said housing. The transmitting optical fibre means receives laser light signals as an input and directs such signals through the window to a scattering volume outside the housing. The receiving optical fibre means receives light signals scattered back through the window from the scattering volume as an input and provides the scattered back signals as an output.

In a preferred embodiment, the apparatus further includes mounting means for securing the housing in an opening extending through a wall of a container for holding the fluid. The first window surface faces inside the container for immersal by the fluid when the housing is so mounted. The securing means includes means for engaging the container wall and the housing to seal the opening against passage of fluid from the container.

The ability of the window to withstand the application of high fluid pressures while immersed particularly facilitates the use of the apparatus to measure asphaltene and wax particle size distributions in petroleum fluids. Firstly, the fact that the outside surface of the window may be immersed allows a scattering volume to be established very close to the window, thereby minimizing the amount of light that will be absorbed by the fluid. Secondly, the tolerance of the Apparatus for high fluid pressure on the housing and the window allows measurements to be made under conditions of pressure comparable to that which may be found in petroleum field reservoirs.

Advantageously, the apparatus may also include heat insulation means inside the housing for providing heat insulation between the transmitting and receiving optical fibre means and the housing. Such insulation means will serve to protect the transmitting and receiving means from excessive heat in cases where the fluid is maintained at a high temperature during measurement of particle size distribution.

The foregoing and other features and advantages of the invention will now be described with reference to the drawings.

DETAILED DESCRIPTION

Figures 1, 5:
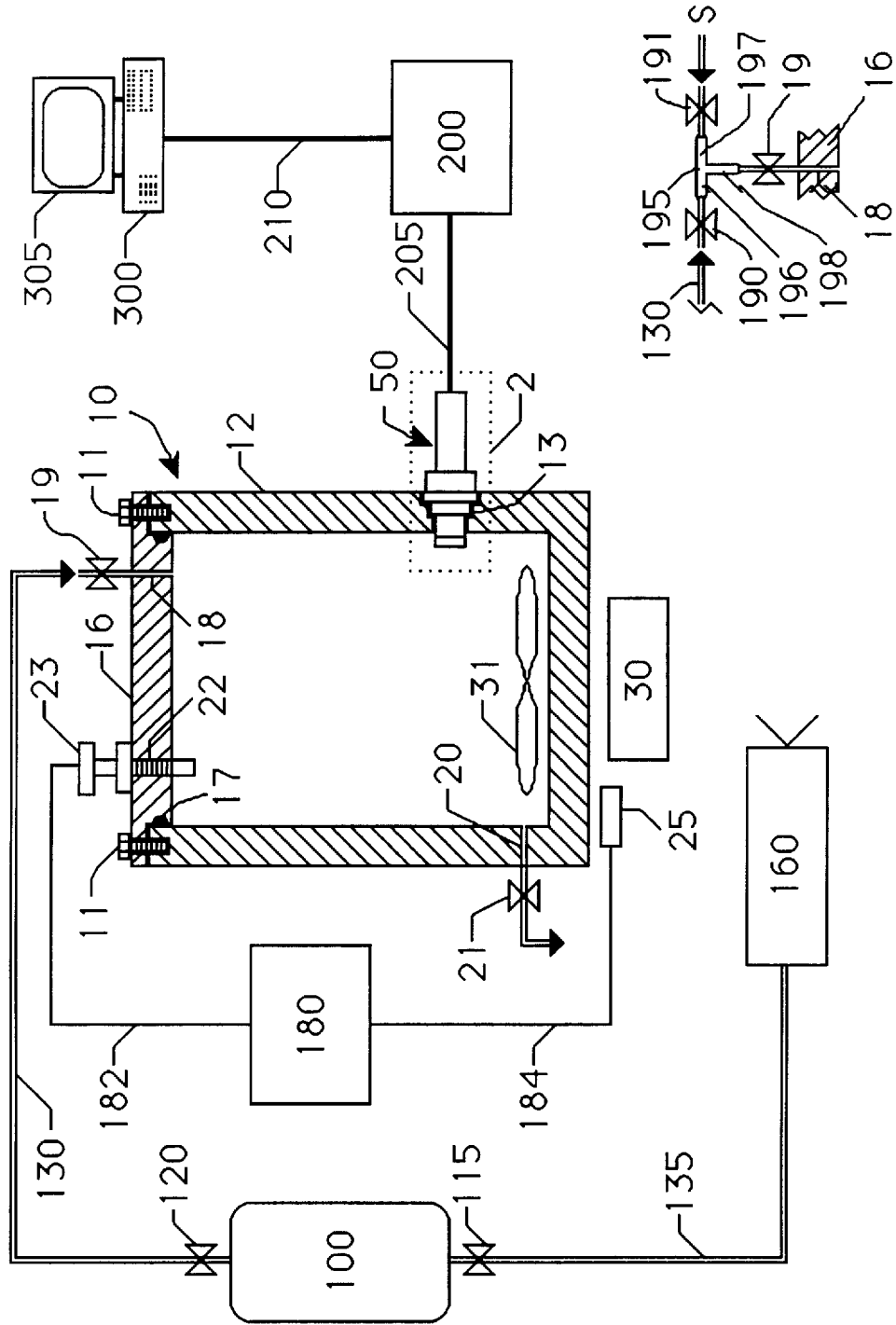
FIG. 1 is a schematic illustration of one embodiment of apparatus for the measurement of particle size distribution in a fluid in accordance with the present invention.
FIG. 5, which is on the same sheet of drawings as FIG. 1, illustrates a variation to the embodiment shown in FIG. 1 which allows for the addition of a solvent prior to the measurement of particle size distribution.

FIG. 1 illustrates a system for measuring sub-micron particle size distribution in petroleum fluids. The system includes a container generally designated 10 for holding the fluid while measurements are being taken (the fluid is not shown), a fibre optic probe generally designated 50 mounted to side wall 12 of the container, a sub-micron particle analyzer 200 connected to probe 50 by means of a fibre optic cable 205 and to a computer 300 by means of an electrical cable 210. Computer 300 includes a display monitor 305.

Sub-micron particle analyzer 200 and associated cables 205, 210 are commercially available instrumentation and related parts available from Brookhaven Instrument Corp. as noted above. Computer 300 may be any suitable PC compatible with the Brookhaven instrument and software (e.g. an IBM 486 DX with math coprocessor).

Figure 2:
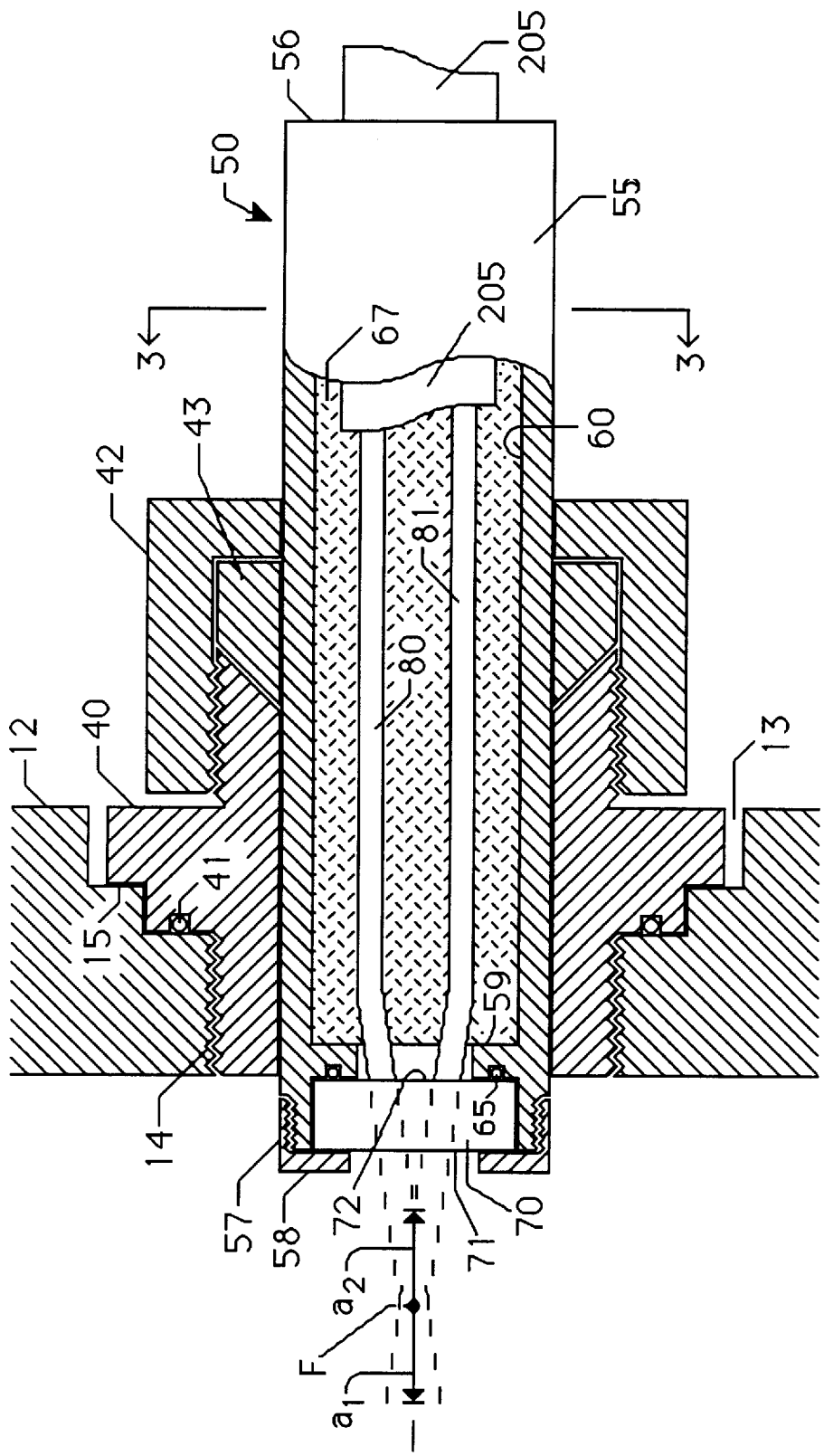
FIG. 2 is a side view, partially sectioned and partially cut away, of a portion of the optical transceiver apparatus shown in FIG. 1.
Figure 3:
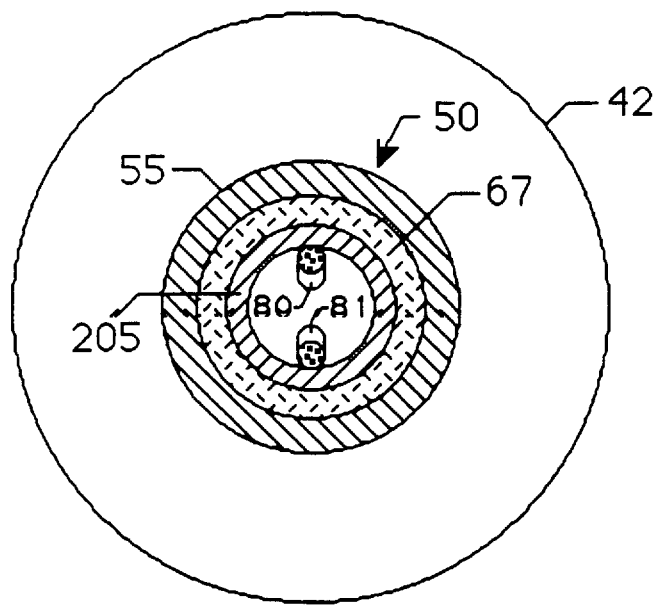
FIG. 3 is a cross-sectional view taken along line 3—3 in FIG. 2.

Probe 50 is an optical transceiver. As best seen in FIGS. 2 and 3 (the former of which shows dotted line area 2 of FIG. 1 in more detail), probe 50 includes an elongated cylindrical housing 55 extending from a first end 56 to a second end 57. A disk shaped optical window 70 is held proximate to end 57 between a pair of flanges 58, 59. A first window surface 71 of window 70 faces outside the housing and a second window surface 72 faces inside the housing. Since the probe may be subjected to relatively high temperatures and fluid pressures, housing 50 is fabricated from stainless steel or the like. Optical window 70 is fabricated from sapphire, and is relatively thick between surfaces 71, 72 to withstand high fluid pressures which may be imposed on surface 71.

To facilitate the placement of window 70 during assembly of probe 50, it will be noted that end 57 of housing 55 has threaded engagement with the remainder of the housing. A sealing ring 65 assists to seal window 70 against the passage of fluid from container 10 into the housing when window surface 71 is immersed by fluid in the container. A sealing means is desirable because, as is discussed in more detail below, the fluid pressure inside container 10 may be substantial.

Sealing ring 65, and other sealing rings which are referred to hereinafter, should be fabricated from a material which does not degrade under the conditions of temperature, pressure and fluid type to which it will be exposed. For most petroleum fluid applications, a synthetic polymer material such as Viton® material should be suitable. For more demanding applications such as petroleum fluid containing hydrogen sulphide other material may be required—for example, a nitrile seal. Viton is a trademark of E.I. DuPont de Nemours and Company, Inc.

Probe 50 also includes a transmitting optical fibre means comprising optical fibre line 80 and a receiving optical fibre means comprising optical fibre line 81. Both lines are a part of cable 205 which extends longitudinally into probe 50 through end 56. Line 80, which includes a portion extending inside housing 55 from end 56 to window 70, receives input laser light signals from particle analyzer 200 and, as indicated by dashed lines in FIG. 2, directs such signals through the window to a scattering volume centered at point F outside the housing. Conversely, line 81, which includes a portion extending inside housing 55 from window 70 to end 56, receives as an input light signals scattered back through the window from the scattering volume, and provides the scattered back signals as an output back to particle analyzer 200.

The portion of cable 205 which extends within housing 55 is insulated from the housing by an annular layer of heat insulating material 67 contained just inside inner wall 60 of the housing. Such insulation may not be required in all situations. However, in situations where probe 50 is exposed to relatively high temperature fluids in container 10, heat insulation may be considered desirable to protect lines 80, 81 or the cable sheath which carries and supports the lines.

With the foregoing construction, probe 50 is particularly adapted for use in conjunction with the measurement of particle size distribution in petroleum fluids. More particularly, end 57 of housing 55 together with outer surface 71 of window 70 may be immersed in the fluid. The fluid may be at relatively high temperature and the fluid pressure acting outside the probe on housing end 71 and window surface 71 may be substantially greater than ambient pressure inside housing 55.

Such immersability is important because it permits a construction where center point F is established relatively close to window surface 71 of window 70. As such, the absorption of light signals by the colored or opaque petroleum fluid will be minimized, and the strength of signals scattered back from the scattering volume will be maximized. Of course, it will be understood that the light signals are required to have a frequency or wavelength which will pass the fluid. In this regard, the approximately 633 nanometer wavelength signals as produced by a Class 3 neon—helium laser as used in the Brookhaven instrument have been found to work suitably for petroleum fluids.

The tolerance for relatively high fluid temperatures and pressures is important because it permits measurements to be taken under conditions of temperature and/or pressure which may be found to exist in a petroleum field reservoir or, as well, under conditions of temperature and/or pressure which may be engineered in the design of recovery and processing systems for handling the fluid when extracted from the reservoir. Preferably, housing 50 and window 70 should be rated for working pressures up to 10,000 psi (about 70 MPa).

The dimensions of probe 50 are generally not critical. However, to put some perspective on a typical size, the main body of housing 55 may have an outside diameter of about 9.525 mm (viz. about 0.375 inches) and an inside diameter of about 6.223 mm (viz. about 0.245 inches). For a 10,000 psi (70 MPa) rating, sapphire window 70 should have a thickness of about 5 mm (viz. about 0.197 inches). Optical lines 80, 81 may be angled at the window to establish a center point F at about 1 mm (viz. about 0.04 inches) and preferably not more than about 2 mm (viz. about 0.08 inches) beyond window surface 71.

Probe 50 is designed to be used in substitution for the probe supplied with the Brookhaven sub-micron particle analyzer referred to above. The principles which underlie the operation of probe 50 are the same as those of the Brookhaven probe. Since such principles are known and will be readily understood by those skilled in the art, they will not be described here in any detail. Essentially, however, and as indicated by broken lines in FIG. 2, the outward path for light from optical line 80 and the inward path for light scattered back to optical line 81 intersect to define a scattering volume centered at point F. With the longitudinal extent indicated by arrows $a_1$, $a_2$, the scattering volume may be seen as the intersection of two cylinders having the transverse cross-sectional area of lines 80, 81.

As best seen in FIG. 2, housing 55 of probe 50 is secured in a partially threaded shouldered opening 13 which extends through side wall 12 of container 10. Threads 14 and two-step shoulder 15 of opening 13 are designed to accept a conventional Swagelok® 'O' ring straight thread connector fitting 40 having an inside diameter corresponding to the outside diameter of housing 55. Swagelok is a trademark of Swagelok, Co. of Solon, Ohio.

When fitting 40 is tightened, sealing ring 41 seals opening 13 against the passage of fluid between wall 12 and the fitting. Housing 55 is tightly secured in the position shown when nut 42 is tightened against compression ring 43. Compression ring 43 then bears against fitting 40 and radially inward against housing 55 to securely grip the housing. The tightened engagement which results also establishes an effective seal against the passage of fluid between housing 55 and the fitting.

Container 10 is a high pressure cylindrical vessel and, as in the case of probe 50, is preferably fabricated from stainless steel rated for working pressures up to about 10,000 psi (70 MPa). Its volume capacity is not critical, but may typically be in the range of 50 cc to 100 cc. As can be seen in FIG. 1, container 10 includes a top 16 which is removably secured to side wall 12 by means of bolts 11. A sealing ring 17 is positioned between top 16 and side wall 12 to provide an effective seal under conditions of high pressure.

Top 16 is removable in order to permit the interior of container 10 to be cleaned and, as well, to allow the positioning of a magnetic stirrer blade 31 inside the container. As shown in FIG. 1, stirrer blade 31 is operated by a magnetic stirrer drive 30 positioned outside the container. Both blade 31 and drive 30 are well known apparatus commercially available from various sources (for example, Fisher Scientific Co. of Pittsburgh, Pa.).

Container 10 further includes an inlet port 18 and inlet valve 19 to permit fluid filling and an outlet port 20 and outlet valve 21 to permit fluid draining. As well, it includes a port 22 to receive a temperature sensor 23. Typically, ports 18, 20 and 22 may have standard NPT (National Pipe Taper) threads (e.g. 0.125 inches or about 3.175 mm) for mounting commercially available pressure fittings such as Swagelok fittings of the type described above.

Temperature sensor 23 is a thermocouple sensor which is part of a means for controlling the temperature of fluid within container 10 and which provides a signal corresponding to temperature controller 180 along line 182. Controller 180 in turn provides an on/off signal along line 184 to an electrical heating means 25 depending upon whether the sensed temperature is above or below a value set with the controller. Such temperature control apparatus is commonplace. One suitable supplier is Omron Electronics Inc. of Schaumburg, Ill.

The system shown in FIG. 1 also includes an arrangement for pumping petroleum fluid from a high pressure capture cell 100 into container 10. Shown in more detail in FIG. 4, capture cell 100 is a conventional device used in the petroleum industry to transfer samples of petroleum fluid recovered from petroleum field reservoirs. Fabricated from stainless steel and preferably rated for working pressures up to about 10,000 psi (70 MPa), it includes a cylindrical housing 101 threadingly capped at opposed ends by caps 103. An opposed pair of valve connectors 102 and an intermediate floating piston 105 are guided within housing 101 along the longitudinal axis of the housing. Seals 106, one each set around the outer perimeter of valve connectors 102, and two set around the outer perimeter of piston 105, prevent the passage of air or fluid between the inside wall of the housing and the piston or valve connectors, as the case may be. Each valve connector 102 includes an inlet/outlet opening 104 for allowing fluid through an associated valve (not shown in FIG. 4) to be directed into or out of the housing, and each includes a threaded end 107 for connection to the valve. When fluid is directed into cell 100 through an inlet/outlet 104, piston 105 will be forced towards the downstream end of housing 101 where it will ultimately bear against the valve connector 102 at the downstream end—the connector in turn bracing against the cap 103 which is at the downstream end.

As shown in FIG. 1, capture cell 100 is connected through valve 120, pipe 130 and valve 19 with inlet port 18 of container 10. As well, the cell is connected through valve 115 and pipe 135 to the output of a high pressure pump 160. However, before the connections to pipes 130 and 135 have been made, the cell must first be filled with a petroleum fluid sample. In practice, this normally will be achieved at a well site where fluid recovered under pressure from an underlying petroleum field reservoir is transferred to the cell. Cell 100, with valves 115 and 120 attached and initially closed, will be placed in fluid connection with the recovery tool. Then, the valves will be opened to permit the cell to fill with fluid via valve 120. Once the cell has been filled, the valves will be closed until the connections shown in FIG. 1 have been made.

Figure 4:
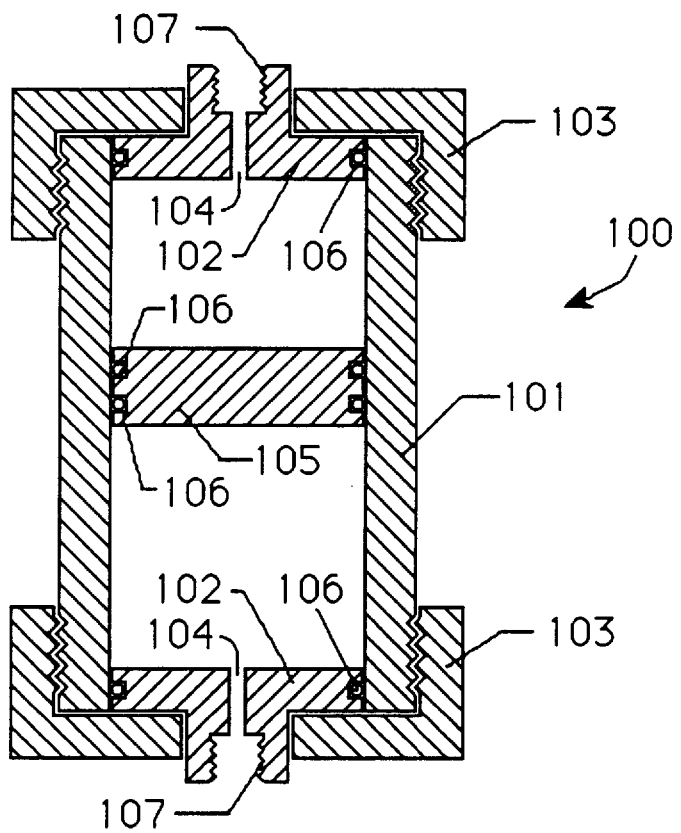
FIG. 4 is a cross-sectional view of a fluid capture cell used with the embodiment shown in FIG. 1.

With fluid in capture cell 100 and valves 115, 120 and 19 open, pump 160 then serves to transfer the fluid from the cell to container 10. As well, pump 160 serves to maintain a desired pressure such as reservoir pressure in the container. However, in order to establish and maintain elevated pressures with a piston driven capture cell as shown in FIG. 4, it will be understood that the initial volume of fluid within the cell must be more than sufficient to fill container 10 and backwards through pipe 130 into housing 101. Otherwise, if piston 105 is driven to the full end of its piston stroke by pump 160, the piston will be unable to apply increasing pump pressure to the fluid. Various commercially available pumps are suitable for this application; for example, the 100D Syringe Pump manufactured or supplied by Isco, Inc. of Lincoln, Nebr.

Thus, it will be apparent that the apparatus shown in the Figures is particularly suitable for the measurement of particle size distribution in petroleum fluids, including the distribution which exists under reservoir conditions. As a first step, a fluid sample is recovered from the reservoir. Then the sample is transferred to capture cell 100 under conditions of pressure prevailing in the reservoir. The cell is then connected in line between pump 160 and container 10, and the sample is then pumped from the cell to the container. In the process, the end of probe 50 which extends inside the container (including outer surface 71 of window 70) becomes immersed by the fluid. The output pressure of the pump is set to correspond to the reservoir pressure. Using the temperature control and heating means described above, the temperature within the container is set to correspond to that of the reservoir. While in the container, the fluid sample is agitated by operation of magnetic stirrer drive 30 and blade 31 to better maintain the suspension of solids in the fluid.

With the end of probe 50 immersed by the fluid sample in container 10, a laser light signal generated by particle analyzer 200 is transmitted over cable 205 (line 80) and directed at the sample from the probe. Light scattered back from the sample is detected by the probe and carried back to particle analyzer 200 over cable 205 (line 81). Particle size distribution is then determined by particle analyzer 200 working with computer 300 in a conventional way Obviously, the pressure of fluid within container 10 need not be the reservoir pressure. Likewise, the temperature need not be the reservoir temperature. Other values, including ambient values, may be established. Further, under any conditions of temperature and pressure which may be established, the apparatus may be used to measure particle size distribution in a petroleum fluid which has been mixed with a solvent. In this regard, it is well known to those skilled in the art that various selected solvents when mixed with a petroleum fluid may have an effect on asphaltene particle size. Depending upon the circumstances, the effect may be one which would serve to enhance petroleum recovery.

One convenient way to measure and study the effect of a selected solvent on asphaltene particle size is illustrated in FIG. 5 which represents a minor modification to the apparatus shown in FIG. 1. Here, a pipe tee 195 and a valve 190 connected to one side 196 of the tee is interposed between pipe 130 and valve 19. The other side 197 of tee 195 is connected through another valve 191 to a source of solvent S (not shown). Stem 198 of the tee is connected to valve 19. When valves 19 and 190 are open and valve 191 is closed, petroleum fluid may be added to container 10 in the same manner as previously described using pump 160. Similarly, when valves 19 and 191 are open and valve 190 is closed, the selected solvent then may be added to container 10 from the solvent source. Of course, the actual amount of solvent will be dependent upon the size of the petroleum fluid sample within container 10 and the desired concentration of solvent in the resulting mixture. As well, in those cases where measurements are to be taken with the contents of container 10 under pressure, it will be understood that the solvent must from source S must be added under pressure to the container. For this purpose, a pumping arrangement the same as that described above for the petroleum fluid may be used.

Thus the apparatus shown in FIG. 1 may be used to examine petroleum fluids and measure particle size distribution under a wide variety of temperature, pressure and/or solvent mixture conditions including not only those which may prevail in a petroleum reservoir but also under controllable conditions which are engineered in recovery and processing systems designed to handle the fluid. Of course, in those situations where the conditions of pressure of immediate interest are ambient conditions, then the use of a high pressure vessel such as container 10 and related equipment may be avoided. However, the use of probe 50 supported by an appropriate means to ensure that outer surface 71 of window 70 is immersed in the fluid when measurements are taken will remain important in order to maximize the amount of light which is scattered back to the probe.

The present invention may be embodied in other specific forms without departing from its spirit or essential characteristics. The apparatus and methodology which have been described are to be considered in all respects only as illustrative and not as restrictive. While such apparatus and methodology are particularly illustrative in relation to the measurement of particle size distribution in petroleum fluids, it will be readily apparent to those skilled in the art that various changes and modifications are possible not only for measurements in relation to petroleum fluids but also for measurements in relation to other fluids including other fluids which are colored or opaque and strongly absorptive of incident light.

Accordingly, the scope of the invention is indicated by the appended claims rather than by the foregoing description. All changes or modifications which come within the meaning and range of equivalency of the claims are considered to be embraced within their scope.

I claim:

1. A method of measuring particle size distribution in a petroleum fluid drawn from a petroleum field reservoir, said method comprising the steps of:

(a) holding said fluid in a container at a pressure controllable up to a pressure approximating that of said reservoir;

(b) directing an incident laser light signal to a scattering volume defined within said contained fluid from an optical transceiver at least partially immersed by said contained fluid; and, (c) detecting light scattered back to said transceiver from said scattering volume in response to said light signal.

2. A method as defined in claim 1, wherein said fluid is held in said container under controlled conditions of temperature.

3. A method as defined in claim 1, wherein said fluid is held in said container under a pressure controlled to approximate that of said reservoir.

4. A method as defined in claim 3, wherein the temperature of said fluid in said container is controlled to approximate that of said reservoir.

5. A method as defined in claim 1, wherein said fluid is mixed with a selected solvent.

6. A method as defined in claim 5, wherein said fluid is held in said container under controlled conditions of temperature.

7. A method as defined in claim 5, wherein said mixture is held in said container under a pressure controlled to approximate that of said reservoir.

8. A method as defined in claim 7, wherein the temperature of said mixture in said container is controlled to approximate that of said reservoir.

9. A method as defined in claim 1, said method further comprising the preliminary steps of:

(a) recovering said sample from said reservoir;

(b) transferring said recovered sample to a fluid capture cell; and, (c) pumping said sample from said capture cell into said container.

10. A method as defined in claim 9, wherein said fluid is mixed with a selected solvent in said container.

11. Apparatus for measuring particle size distribution in a petroleum fluid drawn from a petroleum field reservoir, said apparatus comprising:

(a) a container for holding said fluid;

(b) an optical transceiver;

(c) means for securing said transceiver in an opening extending through a wall of said container in a position for directing an incident laser light signal from said transceiver to a scattering volume defined within said contained fluid and for detecting light scattered back to said transceiver from said scattering volume in response to said light signal, said transceiver being at least partially immersed by said fluid when so secured, said securing means including means for engaging said wall and said transceiver to seal said opening against passage of said fluid from said container; and, (d) means for pressuring said container up to a pressure approximating that of said reservoir.

12. Apparatus as defined in claim 11, including means for controlling the temperature of said fluid within said container.

13. Apparatus as defined in claim 11, wherein said scattering volume has a center point distanced less than 2 mm from a focusing end of said transceiver, said focusing end being immersed by said contained fluid.

14. Apparatus as defined in claim 11, wherein said scattering volume has a center point distanced about 1 mm from a focusing end of said transceiver, said focusing end being immersed by said contained fluid.

\* \* \* \* \*